US008428682B1

(12) United States Patent
Rood et al.

(10) Patent No.: US 8,428,682 B1
(45) Date of Patent: Apr. 23, 2013

(54) WET OR DRY ELECTRODE, OTHER SENSORS, ACTUATORS, OR MARKERS WITH A NOVEL ADHESIVE COLLAR

(75) Inventors: Aaron Rood, Rocky River, OH (US); Greg S. Shaw, University Heights, OH (US); Brian M. Kolkowski, LeRoy, OH (US)

(73) Assignee: Orbital Research Inc., Cleveland, OH (US)

( * ) Notice: Subject to any disclaimer, the term of this patent is extended or adjusted under 35 U.S.C. 154(b) by 1676 days.

(21) Appl. No.: 11/454,520

(22) Filed: Jun. 16, 2006

(51) Int. Cl.
*A61B 5/04* (2006.01)

(52) U.S. Cl.
USPC ............................................ 600/391; 604/21

(58) Field of Classification Search .................. 604/174, 604/180, 289–291, 303–308, 358, 365–378, 604/381, 385.01–385.06, 385.23, 385.31, 604/386, 890.1; 600/372, 386, 391, 392, 600/397, 345–347, 382–385
See application file for complete search history.

(56) References Cited

U.S. PATENT DOCUMENTS

| | | | | |
|---|---|---|---|---|
| 3,713,435 A * | 1/1973 | Szpur | ............................ | 600/392 |
| 3,845,757 A * | 11/1974 | Weyer | ............................ | 600/391 |
| 4,617,935 A * | 10/1986 | Cartmell et al. | ............... | 600/392 |
| 4,763,659 A | 8/1988 | Dunseath, Jr. | | |
| 4,967,740 A | 11/1990 | Riedel | | |
| 5,003,978 A * | 4/1991 | Dunseath, Jr. | ................ | 600/391 |
| 5,215,087 A * | 6/1993 | Anderson et al. | ............. | 600/392 |
| 5,489,624 A * | 2/1996 | Kantner et al. | ............... | 524/376 |
| 5,505,200 A * | 4/1996 | Takaki | ........................... | 600/395 |
| 5,506,059 A * | 4/1996 | Robbins et al. | ............... | 428/457 |
| 5,645,527 A * | 7/1997 | Beck | .............................. | 604/20 |
| 5,916,157 A | 6/1999 | Crosz, Jr. | | |
| 6,330,471 B1 * | 12/2001 | Higo et al. | ...................... | 604/20 |
| 6,341,230 B1 * | 1/2002 | Koike et al. | .................... | 600/392 |
| 6,622,035 B1 * | 9/2003 | Merilainen et al. | ........... | 600/391 |
| 6,640,122 B2 * | 10/2003 | Manoli et al. | ................. | 600/383 |
| 6,782,283 B2 | 8/2004 | Schmidt | | |
| 6,785,569 B2 | 8/2004 | Schmidt | | |
| 7,032,301 B1 | 4/2006 | Schmidt | | |
| 7,032,302 B1 | 4/2006 | Schmidt | | |
| 2004/0138609 A1 * | 7/2004 | Fukuta et al. | .................... | 604/20 |
| 2006/0030767 A1 * | 2/2006 | Lang et al. | .................... | 600/372 |

FOREIGN PATENT DOCUMENTS

WO WO 01/52731 A1 7/2001

OTHER PUBLICATIONS

David D. Cunningham and Michael G. Lowery, Moisture Vapor Transport Channels for the Improved Attachment of a Medical Device to the Human Body, Biomedical Microdevices, 2004, p. 149 to 154, 6:2, Kluwer Academic Publishers, The Netherlands.

B.G. Lapatki, J.P. Van Dijk, M.J. Zwarts, D.F. Stegeman, A thin, flexible multielectrode grid for high-density surface EMG, Journal od Applied Physiology, 2004, p. 327 to 336, J Appl Physio/96, U.S.

* cited by examiner

*Primary Examiner* — Kevin C Sirmons
*Assistant Examiner* — Kami A Bosworth
(74) *Attorney, Agent, or Firm* — Brian Kolkowski

(57) ABSTRACT

The present invention is directed to a device, which can be attached to a subject's skin with an adhesive collar. The device can be a sensor, an actuator or a marker. Preferably, the device is a sensor, and more preferably in the form of a wet or dry electrode sensor, and most preferably, a dry electrode sensor. The invention is used to attach the device to a subject's prepared or unprepared skin so that the device can remain attached to the subject for an extended period of time with minimal skin irritation, breakdown, or re-application, and preferably with no skin irritation, breakdown, or re-application.

5 Claims, 8 Drawing Sheets

WET OR DRY ELECTRODE, OTHER SENSORS, ACTUATORS, OR MARKERS WITH A NOVEL ADHESIVE COLLAR

BACKGROUND OF THE INVENTION

1. Field of the Invention

The present invention is related to a device with an adhesive collar, which can be attached to a subject's skin. The device can be a sensor, an actuator or a marker. Preferably, the device is a sensor, and more preferably in the form of a wet or dry electrode sensor, and most preferably, a dry electrode sensor. The invention is used to attach the device to a subject's prepared or unprepared skin so that the device can remain attached to the subject for an extended period of time with minimal skin irritation, breakdown, or re-application, and preferably with no skin irritation, breakdown, or re-application.

2. Technical Background

Sensors such as electrodes, when attached to a subject's body, must be removed after short periods of use for a variety of reasons. One reason, in the case of a "wet" electrode sensor, the conductive gel or solution that is necessary to enhance conductivity will evaporate over time making the sensor ineffective. Once, evaporated, the sensor can no longer obtain a suitable measurement from the subject, and the sensor either must be replaced, or the electrolytic gel must be re-hydrated or replenished. This requires removal of the electrode, which interrupts continuous data recording, and could ultimately lead to an erroneous test.

Another reason is because the adhesive collar on the electrode or any other device for that matter using such a collar may cause the subject's skin to become irritated, or to even start decomposing, resulting in a rash or reaction on the subject's skin. This can further be enhanced because the clinician or patient usually cannot see beneath the electrode to determine whether there is skin irritation. The patient only becomes aware of the skin irritation after the electrode is removed or when the patient feels itchiness or pain.

In light of the aforementioned disadvantages of current devices, which are placed on a subject's skin using an adhesive collar, it is desirable to create a device which can attach a sensor, actuator, or marker to a subject that can be used for long periods of time without the need to remove it from the subject. Furthermore, it is desirable to develop a way to attach said devices to a subject through a means which is breathable, semi-permeable, waterproof, and/or transparent.

SUMMARY OF THE INVENTION

The present invention is directed to a device, which can be attached to a subject's skin with an adhesive collar. The device can be a sensor, an actuator or a marker. Preferably, the device is a sensor, and more preferably in the form of a wet or dry electrode sensor, and most preferably, a dry electrode sensor. The invention is used to attach the device to a subject's prepared or unprepared skin so that the device can remain attached to the subject for an extended period of time with minimal skin irritation, breakdown, or re-application, and preferably with no skin irritation, breakdown, or re-application.

One embodiment of the present invention includes a device to be attached to a subject's skin comprising a sensor, actuator or marker and an adhesive collar, the adhesive collar comprising a polymer sheet having an upper and a lower surface, an adhesive and a stiffener wherein the adhesive is applied under the lower surface of the polymer sheet and the stiffener is applied above the upper surface of the polymer sheet.

In another embodiment, the present invention includes an electrode to be attached to a subject's skin comprising an electrode sensor, and an adhesive collar, the adhesive collar comprising a polymer sheet having an upper and a lower surface, an adhesive and a stiffener wherein the adhesive is applied under the lower surface of the polymer sheet and the stiffener is applied below the lower surface of the polymer sheet.

In still another embodiment, the present invention includes an electrode to be attached to a subject's skin comprising an electrode sensor comprising a gel, or solution, port for re-hydrating the electrode, and an adhesive collar, the adhesive collar comprising a polymer sheet having an upper and a lower surface, an adhesive and a stiffener wherein the adhesive is applied under the lower surface of the polymer sheet and the stiffener is applied above the upper surface of the polymer sheet.

In even still another embodiment, a device to be attached to a subject's skin comprising a sensor, actuator or marker, and an adhesive collar, the adhesive collar comprising a polymer sheet with a thickness less than about 0.5 mm, and an adhesive, wherein the adhesive is applied the lower surface of the polymer sheet and the stiffener is applied above the upper surface of the polymer sheet.

In even still another embodiment, a device to be attached to a subject's skin comprising a sensor, actuator or marker, and an adhesive collar having an opening, or openings, through which the device is attached, the adhesive collar comprising a polymer sheet having an upper and a lower surface, an adhesive applied under the lower surface of the polymer sheet and a support member about the opening.

Additional features and advantages of the invention will be set forth in the detailed description which follows, and in part will be readily apparent to those skilled in the art from that description or recognized by practicing the invention as described herein, including the detailed description which follows, the claim, as well as the drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

DESCRIPTION OF THE PREFERRED EMBODIMENT

Figure 1:
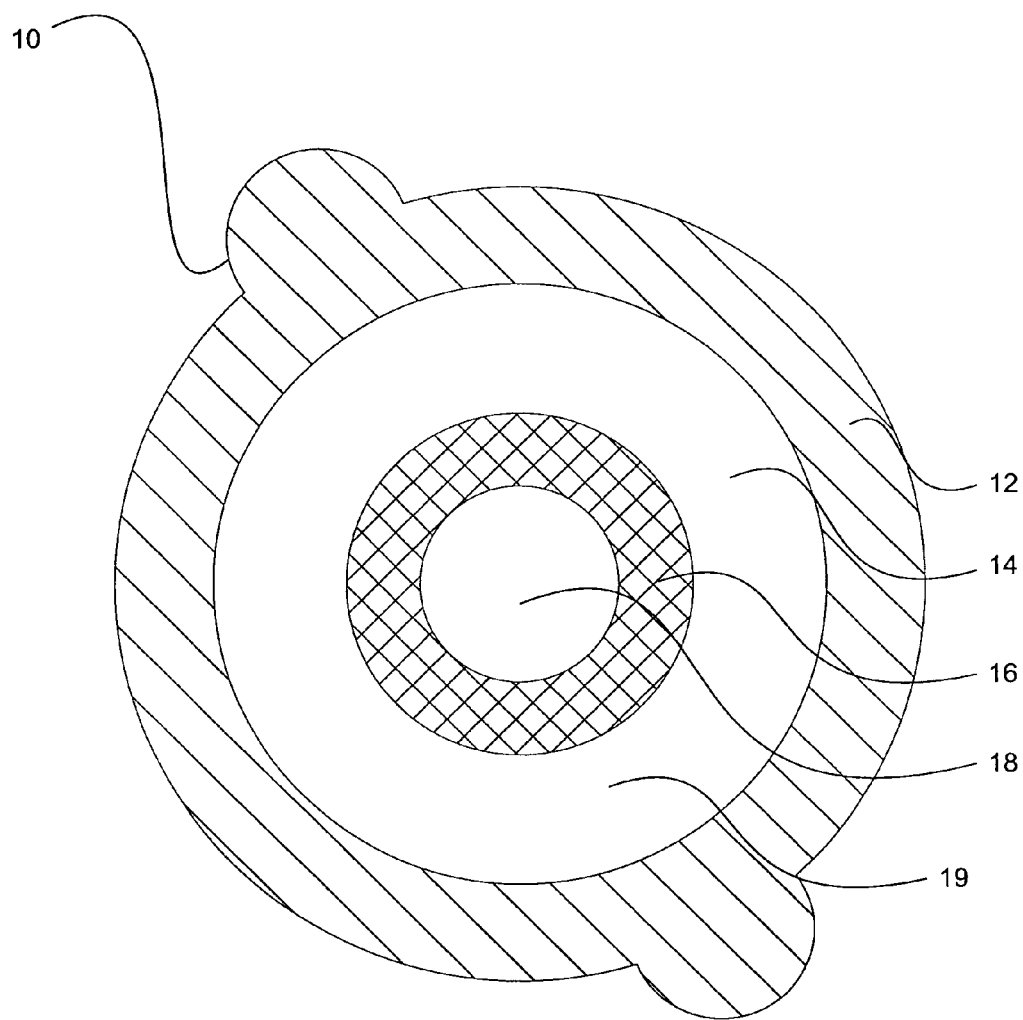
FIG. 1. Top view of the adhesive collar comprising a breathable polymer sheet, and depicting the location of the stiffener, support member, and an opening.

One of the advantages of the present invention is to provide a device, which can be worn by a subject for an extended period of time. The subject for purposes of the present invention is either a human or an animal. Sensors as used for the device of the present invention are devices, which can be used to sense conditions on the surface of the skin, in various layers of the subject's skin or below the subject's skin. Preferably, the sensors are such that they sense a condition and transmit an electrical signal, which is indicative or related to such condition. Sensors can include, but are not limited to pulse oximeters, accelerometers, GPS devices, heat flux sensors, pH sensors, impedance sensors, glucose sensors, respiration sensors, stimulators, thermometers, radiation sensors, blood pressure sensors, hydration sensors, galvanic skin response sensors, pedometers, strain gauges, pressure sensors, force transducers, and alcohol sensors. Preferably, the sensor is a wet or dry electrode. A wet or dry electrode senses an electrophysiological signal, or biopotential, from either the surface of the subject's skin, in the various layers of the subject's skin or below the subject's skin.

Various examples of embodiments of the sensors used in the present invention are described as follows: In one embodiment, the adhesive collar is used to attach a pulse oximeter, which is an external probe that uses light bounced off the blood vessels under the probe to determine level of oxygenation of the hemoglobin in the blood cells, through a computer calculation.

In another embodiment, the adhesive collar is used to attach an accelerometer, which is a transducer that converts mechanical motion into an electrical signal that is proportional to the acceleration value of the motion; it measures acceleration or gravitational force capable of imparting acceleration.

In another embodiment, the adhesive collar is used to attach a GPS unit, any other tracking device, to a subject's skin. GPS refers to satellite-based radio positioning systems that provide 24 hour three-dimensional position, velocity and time information to suitably equipped users anywhere on or near the surface of the Earth (and sometimes off the earth).

In another embodiment, the adhesive collar is used to attach a heat flux sensor to the subject's skin. The heat flux measurement is indicative of the subject's changing body temperature throughout the testing period.

In still another embodiment, the adhesive collar is used to attach a sensor to detect pH levels of perspiration on a subject's skin. pH is a measure of acidity and alkalinity of a solution that is a number on a scale on which a value of 7 represents neutrality, lower numbers indicate increasing acidity, and higher numbers indicate increasing alkalinity. Each unit of change represents a tenfold change in acidity or alkalinity and is the negative logarithm of the effective hydrogen-ion concentration or hydrogen-ion activity in gram equivalents per liter of the solution.

In still another embodiment, a sensor to measure the impedance of a subject's skin is attached to the subject's skin using the adhesive collar. Impedance, is a measure of opposition to a sinusoidal electric current. The concept of electrical impedance generalizes Ohm's law to AC circuit analysis. Unlike electrical resistance, the impedance of an electric circuit can be a complex number.

In still another embodiment, the adhesive collar is used to attach a glucose sensor. Glucose is a simple sugar found in certain foods, especially fruits, and a major source of energy present in human and animal body fluids. The determination of blood glucose is an important diagnostic test in diabetes and other disorders.

In still another embodiment, the adhesive collar is used to attach a respiration sensor. Respiration is the physical and chemical processes by which an organism supplies its cells and tissues with the oxygen needed for metabolism and relieves them of the carbon dioxide formed in energy-producing reactions.

In still another embodiment, the adhesive collar is used to attach a stimulator to a subject's skin to induce muscle movement, growth, and development.

In still another embodiment, the adhesive collar is used to attach a thermometer to measure either body surface temperature or surrounding air temperature.

In still another embodiment, the adhesive collar is used to attach a radiation sensor to a subject's skin to test for radiation levels either within the subject or in the surrounding environment.

In still another embodiment, the adhesive collar is used for attaching a galvanic skin response sensor. The galvanic skin response (GSR) feedback instrument measures skin conductivity from the fingers and/or palms. The GSR is highly sensitive to emotions in some people. GSR feedback has been used in the treatment of excessive sweating (hyperhidrosis) and related dermatological conditions, and for relaxing and desensitization training.

In still yet another embodiment, a blood pressure sensor is attached to a subject's skin using the adhesive collar. The blood pressure sensor is a non-invasive sensor designed to measure human blood pressure. It can be used to measure systolic and diastolic blood pressure utilizing the oscillometric technique. The sensor includes a standard adult size adjustable cuff (27 cm to 39 cm), pump bulb and pressure transducer. Blood pressure is the force of blood exerted on the inside walls of blood vessels. Blood pressure is expressed as a ratio (e.g., 120/80). The first number is the systolic pressure, or the pressure when the heart pushed blood out into the arteries. The second number is the diastolic pressure, or the pressure when the heart rests.

In still another embodiment, the adhesive collar is used to attach a hydration sensor to a subject's skin to test the subject's hydration level.

In another embodiment, the adhesive collar is used to attach a pedometer to a subject. The pedometer or step counter is a device, usually portable and electronic, which counts each step a person makes. Often worn on the belt and kept on all day, it can be observed to see how many steps, thus kilometers/miles the wearer has walked that day, or in this case for an extended period of time without necessary removal.

In still another embodiment, the adhesive collar is used to attach an alcohol sensor to a subject's skin for an extended period of time without removal. The alcohol sensor is used for continuous, passive monitoring of blood alcohol in human subjects transdermally (through the skin) or superficially.

In still another embodiment, the adhesive collar is used for allergy tests in which small disks containing potential allergens are attached to the skin—typically on the back. Typical application time is about 48 hours. The current procedure calls for using a relatively coarse tape where adherence is marginal and decays significantly over that period of time. Substituting the thin, breathable adhesive collar will add to patient comfort an compliance with the 48 hour testing period.

Most preferably, a dry electrode sensor is used in the present invention. When used the dry electrode sensor is attached to the subject's skin using the adhesive collar for continuous or interrupted capture bio-potential signal preferably for ECG, EMG, EEG, or EOG. The dry electrode sensor is a dry physiological recording electrode that can be used with or without skin preparation or the use of electrolytic gels. The dry electrode is comprised of a substrate, a thin metal sheet, a silicon substrate, or a plastic molding or such, having an upper and lower surface, and at least one penetrator which is formed from a conductive coating or material and is protruding from the substrate wherein the penetrator is capable of piercing the stratum corneum or outer layer of the skin, and transmitting an electric potential from the lower layers of the epidermis through the penetrator which can be measured. This application incorporates by reference U.S. patent application Ser. Nos. 10/923,648, 10/874,075, and 09/949,055.

In another preferred embodiment, a wet electrode sensor is attached to the subject's skin using the adhesive collar. The wet electrode sensor can be physiological recording electrodes, which may be placed at one or several locations on the subject's body. In order to obtain a good EEG or brain wave signal it is desirable to have low impedances for the electrodes. Typical EEG electrode connections may have an interfacial impedance between the electrode itself and the skin in the range of from 5,000 to 10,000 ohms. It is in general desirable to reduce such impedance levels to below 2,000 ohms. Therefore a conductive paste, solution, or gel may be applied to the electrode to create a connection with an impedance at or below 2,000 ohms. The conductive paste, solution, or gel eventually evaporates or dehydrates, and must be replaced or rehydrated after an extended period of time. This is a problem which various embodiments of the present invention resolve. Similarly, exposure to water, such as during bathing activities, can dilute the paste or gel compromising the integrity of the electrode system.

In certain embodiments of the present invention, actuators are used as the device. For example, various types of actuators include, but are not limited to, external defibrillator leads, drug injection devices, electrical motors, pneumatic actuators, hydraulic pistons, relays, comb drive, piezoelectric actuators, thermal bimorphs, digital micro-mirror devices, electro-active polymers, small pumps, solenoids, and voice coil actuators.

In certain other embodiments of the present invention, markers are used for the device. Markers are devices that are applied to various locations on the subject's body and used as recording media as part of a higher-level recording system to record, animate, and/or later measure the body's movement.

The various embodiments of the present invention also include an adhesive collar. The adhesive collar preferably is used to mechanically/chemically attach the sensor, actuator, marker or some combination thereof to the subject's skin. The adhesive collar preferably surrounds the device or a portion of the device to ensure good attachment and a good seal to the subject's skin. The adhesive collar is preferably made from adhesive web stock, which is produced in rolls on a release liner. The web stock preferably is a polymer sheet, which can be coated on one or two sides. The polymer sheet has an upper and lower surface. The polymer sheet preferably is a polyethylene, polyolefin, polyester, PVC, or polyurethane. More preferably, the polymer sheet is an elastomer selected from the group consisting of thermoplastic rubbers, vinyl chloride-vinyl acetate resins, acrylic resins, thermoplastic hydrocarbon resins, and urethane resins. The adhesive collar can also be a laminate or have any other structure know to those skilled in the art to provide the properties of the various embodiments of the present invention.

The polymer sheet is preferably elastomeric so it can have better conformity to the subject's skin and to the device. Preferably, also the polymer sheet and its coatings allow it to be breathable so that the adhesive collar and device can remain attached to a subject's skin for a longer period of time than a non-breathable adhesive collar. By breathable it is further preferably meant that some oxygen can permeate through the polymer sheet to allow oxygen to reach the subject's skin. Also preferably, the polymer sheet and its coatings allow moisture between the adhesive on the polymer sheet and the subject's skin to wick away or escape by some other transport mechanism. A measure of the polymer sheet's breathability is its "Moisture Vapor Transmission Rate" (MVTR), which is a measure of the passage of gaseous $H_2O$ through a barrier. Preferably, the MVTR of the polymer sheet is greater than about 100 gms./sq.m/24 hr. More preferably the MVTR is greater than about 200 gms./sq.m/24 hr. Even more preferably, the MVTR is greater than about 400 gms./sq.m/24 hr. Still even more preferably, the MVTR is greater than about 600 gms./sq.m/24 hr. Most preferably the MVTR is greater than about 800 gms./sq.m/24 hr. Preferably the MVTR is measured by a standard method know to those skilled in the art, and more preferably by ASTM F1249-90 (1995) Standard Test Method for Water Vapor Transmission Rate Through Plastic Film and Sheeting.

The polymer sheet is coated on one side with an adhesive. Preferably, the adhesive is a pressure sensitive adhesive. More preferably, the adhesive is a hypoallergenic, pressure sensitive adhesive. Pressure-sensitive adhesives can be any of a variety of materials known for such uses, and are generally applied by, means well known to those skilled in the art to the skin-facing side of the backing. Such adhesives are preferably "hypoallergenic" in that they exhibit acceptable performance in the 21-day Draize test on human subjects. Pressure-sensitive adhesives can be used with primers, tackifiers, plasticizers and other additives such as known to those skilled in the art to provide a better combination of properties of the adhesive with the rest of the pressure sensitive laminate that makes up the adhesive collar. The adhesives are preferably sufficiently tacky in their normal dry state, and have a desired balance of adhesion, cohesion, stretchiness, elasticity and strength for medical use, and more particularly for use on the skin of a subject. Adhesion promoters may also be included in the formulation to promote release from the skin when desirable and to minimize damage to the skin upon removal.

Preferably, the typical adhesion of the tape to stainless steel preferably ranges between about 14.0 to about 60.0 (about 3.9 to about 16.7 N/25 mm), oz./in, more preferably, between about 14.0 to about 41.0 oz./in (about 3.9 to about 11.4 N/25 mm), even more preferably between about 15.0 to about 32.0 oz./in (about 4.2 to about 8.9 N/25 mm), and most preferably between about 19.0 to about 21.0 oz./in (about 5.3 to about 5.8 N/25 mm).

The ideal adhesive thickness (caliper) preferably ranges from about 0.02 to about 0.05 mm, more preferably from about 0.02 to about 0.04 mm, and most preferably from about 0.02 to about 0.03 mm. The polymer sheet thickness is preferably less than about 0.5 mm, more preferably less than about 0.3 mm thick, even more preferably less than about 0.2 mm thick, still even more preferably less than about 0.1 mm and most preferably less than about 0.05 mm thick. The polymer sheet is preferably hypoallergenic, nonporous, not tearable by hand, with a tensile strength preferably ranging from about 3.0 to about 20.0 lbs./in (about 13.3 to about 89 N/25 mm), more preferably, from about 3.0 to about 8.0 lbs./in (about 13.3 to about 35.6 N/25 mm), even more preferably, from about 3.0 to about 6.6 lbs./in (about 13.3 to about 29.4 N/25 mm), and most preferably, from about 3.5 to about 5.0 lbs/in (15.6 to about 22.2 N/25 mm).

The polymer sheet is preferably an opaque polymer, more preferably a semi-translucent polymer, even more preferably a semi-translucent colorless polymer, and most preferably a transparent polymer so that the subject's skin can be observed clearly through the collar. Preferably the Light Transmission Level (LTL), which indicates the amount of visible light that transmits through the polymer sheet, is greater than 20%, more preferably the LTL is greater than 30%, even more preferably the LTL is greater than 40%, even more preferably the LTL is greater than 50%, still even more preferably the LTL is greater than 60%, still even more preferably the LTL is greater than 70%, even more preferably the LTL is greater than 80%, and most preferably the LTL is greater than 90%, Preferably the transparency is measured by a standard method know to those skilled in the art, and more preferably by ASTM D1746-03 Standard Test Method for Transparency of Plastic Sheeting.

The adhesive collar is treated on at least one side with a pressure-sensitive adhesive, preferably the lower surface, while the other side may be treated with a variety of coatings or other layers which may be laminated to, or co-extruded with, the polymer sheet to give the adhesive collar a wide variety of properties.

The adhesive collar also, preferably may or may not have a stiffener, but more preferably the adhesive collar has a stiffener applied to the upper or lower surface. The stiffener can take a variety of forms which may or may not be identical to the size and shape of the adhesive collar. Once applied to the subject, the stiffener should be able to be easily removable from the upper or lower surface of the polymer sheet, if desired. The stiffener aids in application of the device with the adhesive collar to the subject's skin by stiffening the thin polymer sheet so it preferably cannot fold over onto itself. The stiffener preferably covers the size and shape of the adhesive collar and is easily removable, but more preferably the stiffener material only borders the adhesive collar to the extent necessary to prevent the adhesive collar from folding over onto itself. This provides a viewing window that further aids in accurate placement during application of the device and the adhesive collar to the subject's skin. The stiffener can be made from a variety of materials which include, but are not limited to, thin metal foil, paper, coated paper, polymers and the like.

The adhesive collar can take on any shape that will aid in placement and performance of the device on the subject. For example, possible shapes include circles, semi-circles, rectangles, triangles, or any custom shapes that can be created for the specific application area such as a shoulder, elbow, knee, or any other hard-to-place areas on the subject. Preferably, a circular shaped adhesive collar is used. By way of example but not limitation, the adhesive collar can be attached to the device by crimping, use of a fastener, adhesive or any other method or combination thereof for attaching non-connected parts.

The adhesive collar is preferably used in the application of a dry electrode sensor, but if used with a wet electrode sensor, preferably the collar includes a re-hydration port so that the conductive gel, solution, or paste can be re-hydrated automatically or manually without removing the wet electrode sensor and/or adhesive collar. The adhesive collar preferably has a refillable reservoir, which preferably re-hydrates the wet electrode through a capillary action so no pump is necessary. However, if a pump is necessary, it can be attached to the adhesive collar and re-hydrate the wet electrode sensor automatically.

The adhesive collar also preferably has a support member applied to the upper or lower surface. The support member can take a variety of forms. This support member may or may not be made up of the same materials as the stiffener. The support member may or may not be removable, but is preferably not removable and is used as a reinforcement or support around the area where the adhesive collar attaches to the device. The support member ideally prevents normal or shear stresses created by the device from tearing or deforming the polymer sheet used in the adhesive collar.

Preferably, the device, with the adhesive collar, can remain on the patient's skin for over 24 hours, more preferably for over 36 hours, even more preferably for over 48 hours, and most preferably for over 72 hours.

Referring now to FIG. 1, FIG. 1 is a top view of the adhesive collar 10, comprising a breathable polymer sheet 14, and further depicting the location of the stiffener 12, support member 16, and opening 18. The stiffener 12, which aids in application of the adhesive collar to the subject's skin, is easily removable, and prevents the polymer sheet 14 from folding onto itself (prior to application) as the device applied to the subject. The stiffener 12 is applied to the upper surface of the polymer sheet 14. The adhesive collar 10 in this embodiment also provides for a support member 16, which provides support for the device 20 which attaches to the adhesive collar 10, and prevents the forces from attachment, application or use of the device from tearing or deforming the polymer sheet 14 at the opening 18. In this embodiment a window 19 is formed between the support member 16 and the stiffener 12 through which the subject's skin can be viewed.

Figure 2:
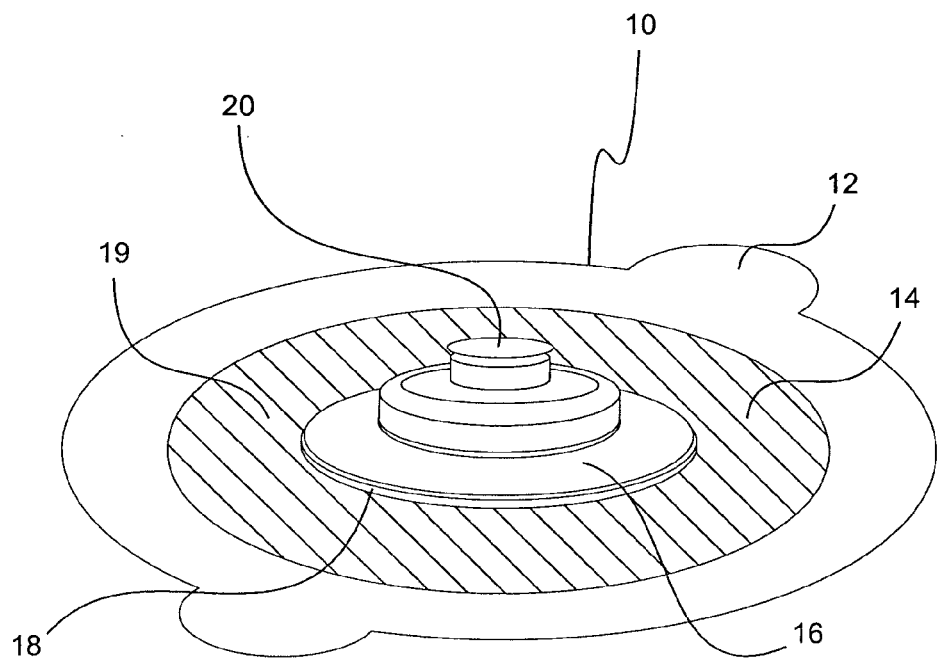
FIG. 2. Top isometric view of the adhesive collar showing the location of the stiffener and the placement of the device through the opening in the adhesive collar.

FIG. 2 is a top isometric view of the adhesive collar 10 depicting the location of the stiffener 12 and the placement of the device 20 through the opening 18 in the polymer sheet 14. The device 20 is attached to the adhesive collar 10 by crimping (not shown). The adhesive collar 10 of the device 20 also comprises a transparent viewing window 19, which provides for better placement of the device 20.

Figure 3:
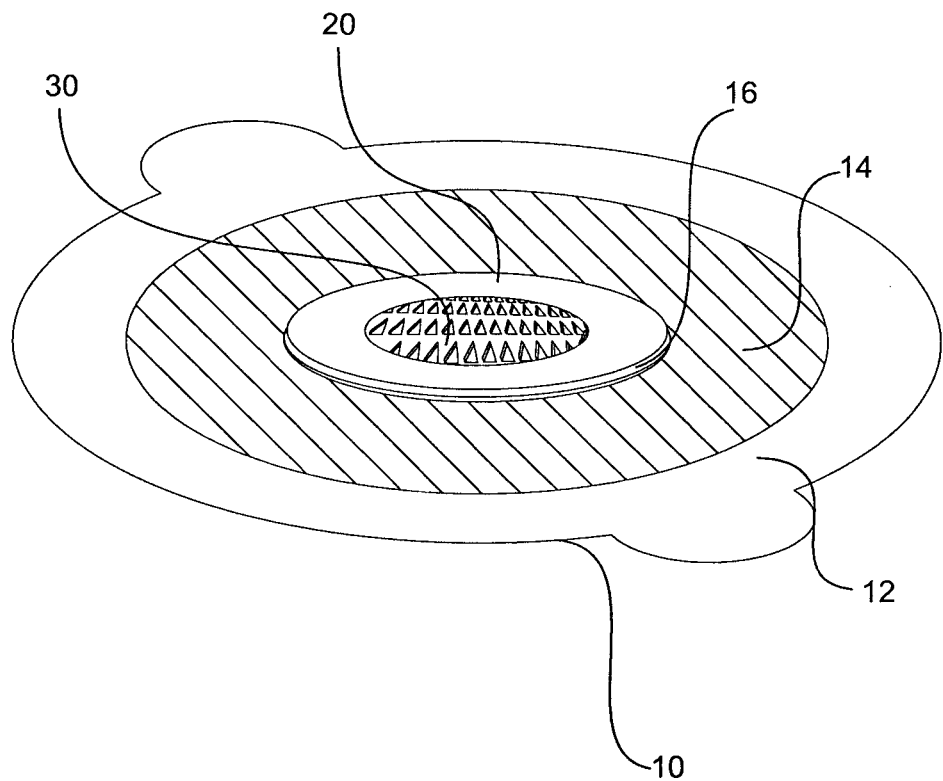
FIG. 3. Bottom isometric view of the adhesive collar also depicting the location of the device through the opening in the adhesive collar, and showing the penetrator features of a dry electrode device.

FIG. 3. is a bottom isometric view of the adhesive collar 10 depicting the location of the device 20 through the opening 18, and showing penetrator features 30 of a dry electrode device 20. The locations of the stiffener 12 and support member 16 are viewable through the polymer sheet 14. In this embodiment, the device 20 is adhesively attached to the adhesive collar 10 with a structural adhesive (not shown).

Figure 4:
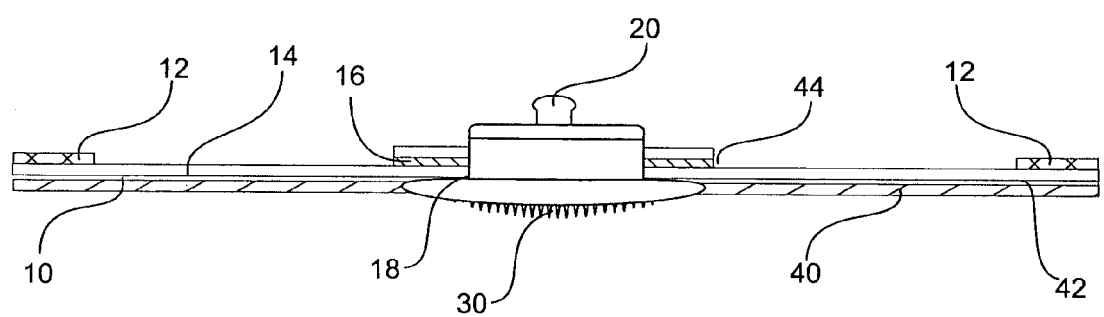
FIG. 4. Cross-sectional view showing the various layers of one embodiment of the adhesive collar with a device through the hole location in the adhesive collar.

FIG. 4. is a cross-sectional view of a device further showing the various layers of the adhesive collar 10. The polymer sheet 14 has the stiffener 12 and support member 16 applied to the upper surface, the adhesive coating 42, is applied to the lower surface, and the release liner 40 is applied below the adhesive which is applied to the lower surface. The dry electrode device 20 is crimped 44 to the adhesive collar 10, with the dry electrode penetrators 30, underneath the opening 18.

Figure 5:
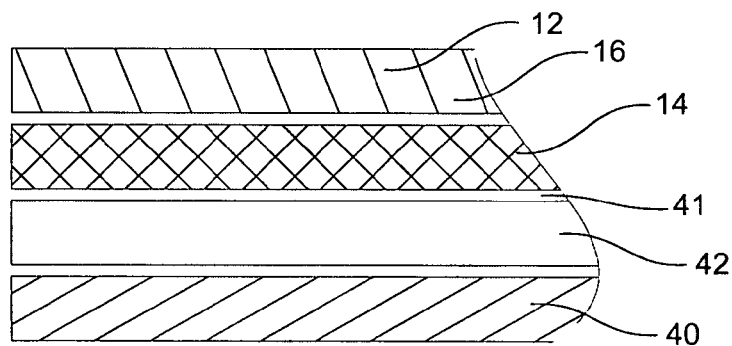
FIG. 5. Cross-sectional, schematic view showing the various layers of another embodiment of the adhesive collar.

FIG. 5. is a cross-sectional, schematic view showing the various layers of the adhesive collar 10. The stiffener 12 and the support member 16 make up the top layer, and are applied to the upper surface of the polymer sheet 14. The adhesive 42 is applied to the lower surface 41 of the polymer sheet 14, with a release liner 40 being applied on the bottom surface of the adhesive 42. The thicknesses of these layers are not to scale.

Figure 6:
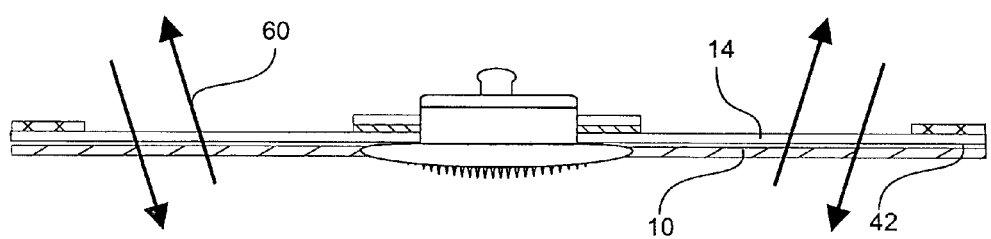
FIG. 6. Cross-sectional view of one embodiment of a device of the present invention showing airflow (breathability) of the adhesive collar 10.
Figure 7:
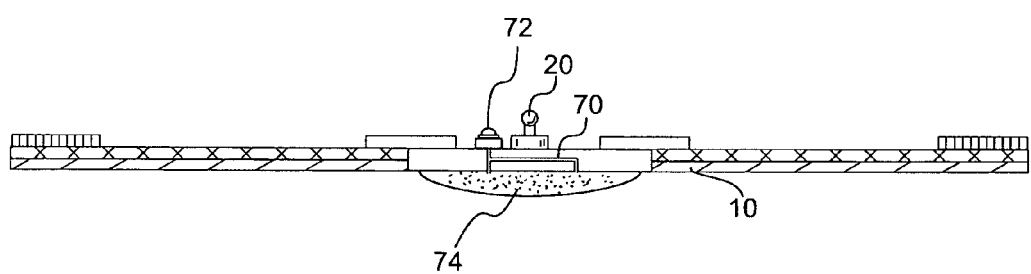
FIG. 7. Cross-sectional view of one embodiment of a wet electrode of the present invention with a re-hydration reservoir for re-hydrating the wet electrode.

FIG. 6. is a cross-sectional view of one embodiment of a device of the present invention showing airflow (breathability) of the adhesive collar 10. The polymer sheet 14 and adhesive 42 combination is one that is breathable to allow oxygen, and/or moisture, to pass through 60 so that device can remain attached to the subject for an extended period of time with minimal skin irritation, breakdown, or re-application, FIG. 7. is a cross-sectional view of a wet electrode device 20 with a re-hydration reservoir 70 for re-hydrating the conductive gel or solution that is used to reduce impedance when a wet electrode sensor is used with the adhesive collar 10. The reservoir 70 in this embodiment is a flexible reservoir that can be squeezed by the subject to force a re-hydrating fluid through a port 72 to re-hydrate the actual wet electrode 74.

Figure 8:
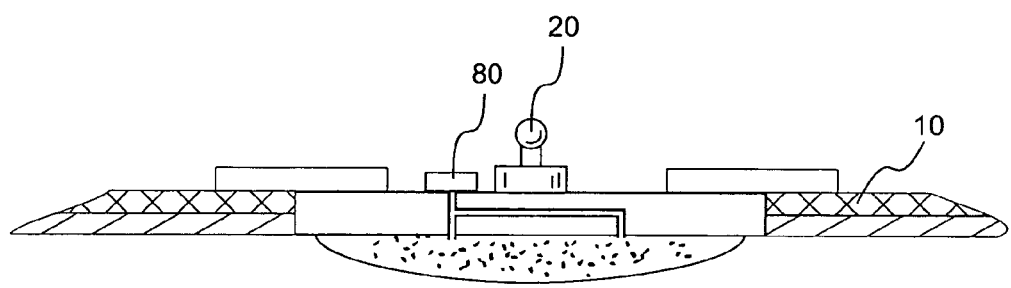
FIG. 8. Cross-sectional view of one embodiment of a wet electrode of the present invention having a re-hydration port.

FIG. 8. is a cross-sectional view of the adhesive collar 10 with a wet electrode device 20 and a reservoir 70 and port 72. The reservoir port 72 allows for the connection of a tube or pump (not shown) to the device 20, through a connector 80, to re-hydrate the conductive gel or solution used with the wet electrode. It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

We claim:

1. A dry physiological electrode with adhesive collar to be attached to a subject's skin comprising
   a dry electrode sensor comprising a substrate having an upper and lower surface and at least one penetrator(s) protruding from the lower surface of the substrate;
   an adhesive collar for attaching the dry electrode sensor to a subject's skin, the adhesive collar comprising a breathable polymer sheet having an upper and a lower surface, and an adhesive
   wherein the moisture vapor transmission rate (MVTR) of the breathable polymer sheet is greater than about 100 g/sq.m./24 hrs.

2. The dry electrode sensor in claim 1, wherein the polymer sheet is less than about 0.5 mm thick.

3. The dry electrode sensor in claim 1, wherein the adhesive collar further comprises a stiffener, the adhesive is applied under the lower surface of the polymer sheet and the stiffener is applied above the upper surface of the polymer sheet.

4. The dry electrode sensor in claim 1, wherein the polymer sheet comprises a urethane.

5. The dry electrode sensor in claim 1, wherein the polymer sheet is transparent and the adhesive collar provides a window to assist in placement of the dry electrode sensor.

\* \* \* \* \*